United States Patent
Lambert et al.

(10) Patent No.: US 10,842,464 B2
(45) Date of Patent: Nov. 24, 2020

(54) APPARATUS AND METHOD FOR DETERMINING BLOOD FLOW VELOCITY

(71) Applicant: KONINKLIJKE PHILIPS N.V., Eindhoven (NL)

(72) Inventors: Nicolaas Lambert, Waalre (NL); Bart Kroon, Eindhoven (NL); Alexander Franciscus Kolen, Eindhoven (NL); Denny Mathew, Eindhoven (NL); Rick Bezemer, Amsterdam (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 382 days.

(21) Appl. No.: 15/574,164

(22) PCT Filed: May 17, 2016

(86) PCT No.: PCT/EP2016/060950
§ 371 (c)(1),
(2) Date: Nov. 15, 2017

(87) PCT Pub. No.: WO2016/188784
PCT Pub. Date: Dec. 1, 2016

(65) Prior Publication Data
US 2018/0098747 A1 Apr. 12, 2018

(30) Foreign Application Priority Data

May 28, 2015 (EP) .................................... 15169654

(51) Int. Cl.
*A61B 8/06* (2006.01)
*A61B 5/024* (2006.01)
(Continued)

(52) U.S. Cl.
CPC .............. *A61B 8/065* (2013.01); *A61B 5/024* (2013.01); *A61B 5/725* (2013.01); *A61B 8/06* (2013.01);
(Continued)

(58) Field of Classification Search
None
See application file for complete search history.

(56) References Cited

U.S. PATENT DOCUMENTS

| 3,974,692 A | 8/1976 | Hassler | |
| 4,630,612 A * | 12/1986 | Uchida | A61B 8/06 |
| | | | 600/441 |

(Continued)

FOREIGN PATENT DOCUMENTS

| CN | 103479396 | 1/2014 |
| EP | 0321717 | 6/1989 |
| WO | 2008/012820 | 1/2008 |

OTHER PUBLICATIONS

Anchan, R. (2011). Estimating pulse wave velocity using mobile phone sensors. Retrieved from https://ro.ecu.edu.au/theses_hons/7 (Year: 2011).*

(Continued)

*Primary Examiner* — Katherine L Fernandez
*Assistant Examiner* — Yi-Shan Yang

(57) ABSTRACT

Apparatus and method comprising an ultrasound transmitter, for placement at a first location on the body of a subject, to emit an ultrasound pulse; an ultrasound receiver, for placement at a second location on the body, to detect an emitted ultrasound pulse; and a controller in communication with the transmitter and receiver. The controller causes an ultrasound pulse to be emitted by the transmitter; receives a measurement signal from the receiver; determines, based on the received measurement signal, a time of arrival at the receiver, $T_1$ s of a first part of the emitted ultrasound pulse;

(Continued)

determines, based on the received measurement signal, a time of arrival at the receiver, $T_2$, of a second part of the ultrasound pulse; and calculates, using $T_1$ and $T_2$, a flow velocity of blood in a blood vessel between the first location and the second location.

17 Claims, 2 Drawing Sheets

(51) Int. Cl.
   *A61B 5/00* (2006.01)
   *A61B 8/15* (2006.01)
   *A61B 8/00* (2006.01)
   *A61B 8/08* (2006.01)

(52) U.S. Cl.
   CPC .............. *A61B 8/15* (2013.01); *A61B 8/4236* (2013.01); *A61B 8/4477* (2013.01); *A61B 8/5223* (2013.01); *A61B 8/54* (2013.01); *A61B 8/56* (2013.01); *A61B 8/58* (2013.01)

(56) References Cited

U.S. PATENT DOCUMENTS

| | | | |
|---|---|---|---|
| 4,944,189 A * | 7/1990 | Nakajima | A61B 8/06 600/437 |
| 5,373,848 A | 12/1994 | Melton | |
| 6,565,513 B1 | 5/2003 | Phillips | |
| 7,469,598 B2 | 12/2008 | Shkarlet | |
| 2003/0100833 A1* | 5/2003 | He | A61B 8/488 600/446 |
| 2008/0119741 A1* | 5/2008 | Friedman | A61B 5/02007 600/485 |
| 2008/0249379 A1* | 10/2008 | Furman | A61B 5/0031 600/301 |
| 2009/0270695 A1 | 10/2009 | McEowen | |
| 2012/0203113 A1 | 8/2012 | Skerl | |
| 2013/0172691 A1* | 7/2013 | Tran | A61B 8/488 600/301 |
| 2013/0274620 A1* | 10/2013 | Zhang | A61B 5/02007 600/490 |
| 2016/0345930 A1* | 12/2016 | Mizukami | A61B 8/02 |
| 2017/0367595 A1* | 12/2017 | Leem | A61B 5/02 |

OTHER PUBLICATIONS

Hein, et al.: "Current Time-Domain Methods for Assessing Tissue Motion by Analysis from Reflected Ultrasound Echoes—A Review", IEEE Transactions on Ultrasonics, Ferroelectrics, and Frequency Control, vol. 40, No. 2, Mar. 1993.

* cited by examiner

APPARATUS AND METHOD FOR DETERMINING BLOOD FLOW VELOCITY

CROSS REFERENCE TO RELATED APPLICATIONS

This application is the U.S. National Phase application under 35 U.S.C. § 371 of International Application No. PCT/EP2016/060950, filed May 17, 2016, published as WO 2016/188784 on Dec. 1, 2016, which claims the benefit of European Patent Application Number 15169654.9 filed May 28, 2015. These applications are hereby incorporated by reference herein.

TECHNICAL FIELD OF THE INVENTION

The invention relates to an apparatus and method for determining blood flow velocity, and in particular to an apparatus and method for measuring the velocity of blood flowing in a blood vessel of a subject.

BACKGROUND TO THE INVENTION

From a clinical point-of-view, the best indication of the hemodynamic status of a patient is provided by the amount of blood the heart pumps, per beat (stroke volume) and per minute (cardiac output). However, these parameters are difficult to measure, either invasively or non-invasively, and there is no widely-accepted "gold standard" measurement technique.

Stroke volume and cardiac output can be measured invasively, e.g. using thermo-dilution or indicator-dilution techniques. However, these methods have several drawbacks. They cannot be used continuously, which makes them unsuitable for monitoring the effect of an intervention on the hemodynamic status of a patient. Furthermore, they provide a result which is an average over many heartbeats, meaning that information on the beat-to-beat variations in stroke volume is lost. Such variations are important in assessing the volume status and fluid responsiveness of a patient.

Cardiac output can be estimated non-invasively using gas rebreathing techniques (which suffer from the same shortcomings as the invasive methods described above), using thoracic bio-impedance (inaccurate and highly sensitive to electrode placement and patient movement), and/or by pulse contour analysis on peripheral pulse pressure waves, measured for example using a photoplethysmograph (PPG) sensor in combination with a pressure cuff around the finger (very sensitive to peripheral vasoregulation in response to changes in ambient temperature, posture, and volume status).

The flow velocity of blood in the aorta provides a reliable surrogate for stroke volume and cardiac output. The rise in blood flow velocity through the aorta with each heartbeat is indicative of the cardiac contractility and ejected stroke volume, because the stiffness of the aorta does not change significantly over a measurement period of several hours or days, or even weeks or months (unlike the peripheral vasculature, which can change tone every minute). However, conventional techniques for measuring aortic blood flow velocity involve using a catheter inside the aorta itself or an imaging ultrasound probe inside the esophagus, both of which are highly invasive.

Document U.S. Pat. No. 6,565,513 describes a device that can measure aortic blood flow velocity from outside the body. The device comprises an ultrasound transducer which is placed on the chest and aimed to emit ultrasound at the ascending aorta. The flow velocity of blood in the aorta is determined based on the Doppler shift in the reflected ultrasound detected by the transducer. This system requires accurate aiming of the ultrasound transducer, which must be done manually by a medical professional. Furthermore, the use of Doppler imaging means that sophisticated processing capabilities are required, limiting how cost-effective the system can be.

There exists, therefore, a need for a non-invasive, cost-effective and easy-to-use system for determining the hemodynamic status of a subject. Preferably such a system would be suitable for continuous monitoring, and would be capable of providing information about beat-to-beat variations in stroke volume and/or aortic blood flow velocity.

SUMMARY OF THE INVENTION

According to a first aspect of the invention, there is provided an apparatus for measuring the velocity of blood flowing in a blood vessel of a subject. The apparatus comprises an ultrasound transmitter, for placement at a first location on the body of a subject, and arranged to emit an ultrasound pulse; an ultrasound receiver, for placement at a second location on the body of the subject, and arranged to detect an ultrasound pulse emitted by the transmitter; and a controller in communication with the transmitter and the receiver. The controller is arranged to cause an ultrasound pulse to be emitted by the transmitter; receive a measurement signal from the receiver corresponding to a detected ultrasound pulse; determine, based on the received measurement signal, a time of arrival at the receiver, $T_1$, of a first part of the emitted ultrasound pulse; determine, based on the received measurement signal, a time of arrival at the receiver, $T_2$, of a second part of the emitted ultrasound pulse; and calculate, using $T_1$ and $T_2$, a flow velocity of blood in a blood vessel located between the first location and the second location.

In some embodiments the first part of the emitted ultrasound pulse corresponds to at least part of a first rising edge of an envelope of the received measurement signal and the second part of the emitted ultrasound pulse corresponds to at least part of a main peak of the envelope.

In some embodiments determining $T_1$ comprises determining the earliest time at which the envelope of the received measurement signal equals a first predefined threshold amplitude and determining $T_2$ comprises determining the earliest time at which the envelope equals a second predefined threshold amplitude.

In some embodiments the first predefined threshold amplitude corresponds to a first percentage of the maximum amplitude of the received measurement signal and the second predefined threshold amplitude corresponds to a second, larger, percentage of the maximum amplitude.

In some embodiments the flow velocity is calculated from:

$$\frac{(ToF_2 - ToF_1)c}{ToF_2} = \frac{vc}{(c+v)} \approx v$$

where $ToF_1$ is the time of flight of the first part of the ultrasound pulse and is given by $$ToF_1 = \frac{L}{c+v},$$

ToF$_2$ is the time of flight of the second part of the ultrasound pulse and is given by $$ToF_2 = \frac{L}{c},$$

L is the length of the ultrasound path between the transmitter and the receiver, v is the flow velocity, and c is the speed of sound in soft tissue. In some embodiments the flow velocity is calculated from:

$$(T_2 - T_1)\frac{c^2}{L} = \frac{vc}{(c+v)} \approx v.$$

In some embodiments the controller is arranged to cause an ultrasound pulse to be emitted by the transmitter at regular intervals; receive a measurement signal from the receiver, determine $T_1$ and $T_2$, and calculate a flow velocity, in respect of each emitted ultrasound pulse; and generate a time-dependent flow velocity signal based on the calculated flow velocity values.

In some embodiments the controller is further arranged to receive a heartbeat rhythm signal for the subject; and filter the flow velocity signal to extract variations synchronous with the received heartbeat rhythm signal using a band pass filter.

In some embodiments the controller is further arranged to fit the flow velocity signal to a model.

In some embodiments the controller is further arranged to receive posture information for the subject; and correct the flow velocity signal based on the received posture information.

In some embodiments the controller is further arranged to calculate a stroke volume and/or a cardiac output of the subject, based on the calculated blood flow velocity.

In some embodiments one or more operational parameters of the transmitter and/or receiver is automatically adjustable by the controller. In some such embodiments the controller is further arranged to perform a calibration process comprising adjusting one or more operational parameters of the transmitter and/or the receiver; measuring one or more attributes of the signal detected by the receiver; and selecting a value for each of the one or more operational parameters based on the measured one or more attributes.

In some embodiments each of the transmitter and the receiver comprises circuitry embedded in an adhesive patch for adhering to the skin of the subject.

There is also provided, according to a second aspect of the invention, a controller for the apparatus of the first aspect. The controller comprises a communications interface for enabling communication between the controller and ultrasound transmitter and between the controller and an ultrasound receiver; and a processing unit. The processing unit is arranged to output a control signal to an ultrasound transmitter to cause the ultrasound transmitter to emit an ultrasound pulse; receive a measurement signal from an ultrasound receiver, corresponding to a detection by the receiver of the emitted ultrasound pulse; determine, based on the received measurement signal, a time of arrival at the receiver, $T_1$, of a first part of the emitted ultrasound pulse; determine, based on the received signal, a time of arrival at the receiver, $T_2$, of a second part of the emitted ultrasound pulse; and calculate, using $T_1$ and $T_2$, a flow velocity of blood in an blood vessel located between the transmitter and the receiver.

There is also provided, according to a third aspect of the invention, a method of measuring the velocity of blood flowing in a blood vessel of a subject. The method comprises causing an ultrasound pulse to be emitted from an ultrasound transmitter at a first location on the body of the subject; receiving a measurement signal from an ultrasound receiver at a second location on the body of the subject, the received signal corresponding to a detection by the receiver of the emitted ultrasound pulse; determining, based on the received measurement signal, a time of arrival at the receiver, $T_1$, of a first part of the emitted ultrasound pulse; determining, based on the received measurement signal, a time of arrival at the receiver, $T_2$, of a second part of the emitted ultrasound pulse; and calculating, using $T_1$ and $T_2$, a flow velocity of blood in an blood vessel located between the first location and the second location.

In some embodiments the blood vessel comprises the descending aorta.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
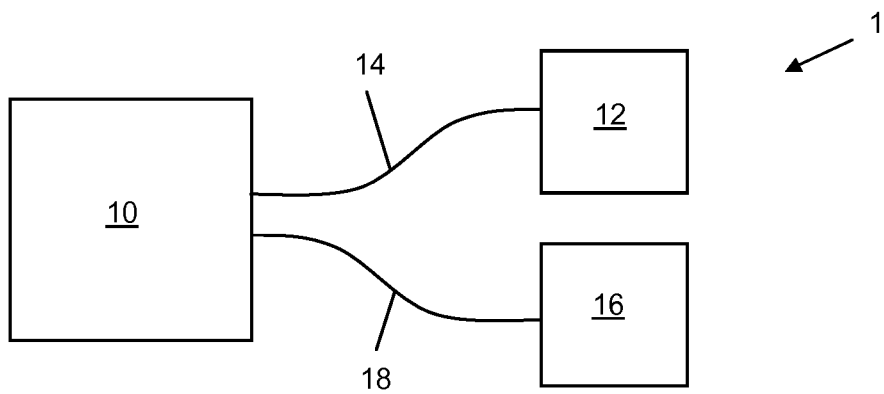
FIG. 1 is an illustration of an apparatus for measuring the velocity of blood flowing in a blood vessel of a subject according to an embodiment.

FIG. 1 shows an apparatus 1 for measuring the velocity of blood flowing in a blood vessel of a subject according to an embodiment of the invention. The apparatus 1 comprises a controller 10 that is in communication with a transmitter 12 via a communications link 14 and that is in communication with a receiver 16 via a communications link 18. The communications links 14, 16 may be any combination of wired or wireless. In embodiments in which both communications links are wired, the length of the wires is effective to permit the transmitter 12 and the receiver 16 to be arranged on a subject such that a blood vessel in which it is desired to measure blood flow velocity is located between the transmitter 12 and the receiver 16. For example, in an embodiment in which the apparatus 1 is for measuring the velocity of blood flowing in the descending aorta, the transmitter 12 is configured for placement on or near the neck of the subject and the receiver 16 is configured for placement on or near the back of the subject.

The transmitter 12 is arranged to emit pulsed ultrasound, e.g. in response to a control signal received from the controller 10. Blood has a relatively low damping coefficient (0.2 dB/(MHz·cm)) compared to surrounding soft tissue (0.54 dB/(MHz·cm)) and muscle (1.1 dB/(MHz·cm)), whilst bone has a dramatically higher damping coefficient. This means that for ultrasound having a frequency of the order of a few MHz, the part of the received signal which has passed through blood will be significantly enhanced compared to the part of the signal which has passed through surrounding tissue. As such, in preferred embodiments the transmitter is arranged to emit ultrasound at a frequency in the range of 1-10 MHz. The frequency at which the pulses are emitted (i.e. the repetition frequency of the pulses) is preferably in the range 10 Hz to 10 kHz. The frequency at which the pulses are emitted is preferably sufficiently high to track blood flow variations caused by the cardiac cycle and to enable good signal-to-noise averaging, but sufficiently low to avoid the rising edge of a newly-received pulse signal overlapping the tail of a previously received pulse signal. If such overlapping occurs it is more difficult to accurately determine the arrival time, although this can be partially overcome by using suitable pulse patterns and correlation techniques.

In some embodiments the transmitter 12 is a wide-angle transmitter. In some embodiments the transmitter 12 is a 1-D transmitter. In some embodiments the output of the transmitter 12 is optimizable, e.g. by means of the transmitter having electronic beam steering and/or focusing capabilities. In some embodiments the transmitter 12 comprises a transceiver, such that it is able to receive ultrasound as well as transmit ultrasound. The receiver 16 is arranged to detect an ultrasound pulse emitted by the transmitter. In some embodiments the receiver 16 is arranged to output a detected signal to the controller 10. In some embodiments the receiver 16 is a wide-angle receiver. In some embodiments the receiver 16 is a 1-D receiver. In some embodiments the detection field of the receiver 16 is optimizable, e.g. by means of the receiver having electronic steering and/or focusing capabilities. In some embodiments the receiver 16 comprises a transceiver, such that it is able to transmit ultrasound as well as receive ultrasound. In some embodiments the transmitter 12 and receiver 16 have a common electronic time base (e.g. established via the communications links 14, 18 to the controller). In some embodiments the transmitter 12 and receiver 16 comprise circuits embedded in adhesive patches for direct application to the skin of a subject.

The controller 10 is arranged to cause an ultrasound pulse to be emitted by the transmitter 12, e.g. by sending a control signal to the transmitter 12 via the communications link 14. The controller 10 is also arranged to receive, e.g. via the communications link 18, a signal from the receiver 16 corresponding to an ultrasound pulse detected by the receiver. The controller 10 is further arranged to determine, based on the signal received from the receiver 16, a time of arrival at the receiver, $T_1$, of a first part of an ultrasound pulse emitted by the transmitter 12 and subsequently detected by the receiver 16, and a time of arrival at the receiver, $T_2$, of a second part of the same ultrasound pulse. The controller is further arranged to calculate, using $T_1$ and $T_2$, a flow velocity of blood in a blood vessel located between the transmitter 12 and the receiver 16. In some embodiments the controller 10 is arranged to filter the received signal. In some embodiments the controller 10 is arranged to perform envelope-level signal processing on the received signal. In some embodiments the controller 10 is arranged to generate a time-dependent flow velocity signal based on multiple calculated flow velocity values. In some embodiments the controller 10 is arranged to process the flow velocity signal, e.g. by filtering, correcting, or fitting to a model.

Figure 2:
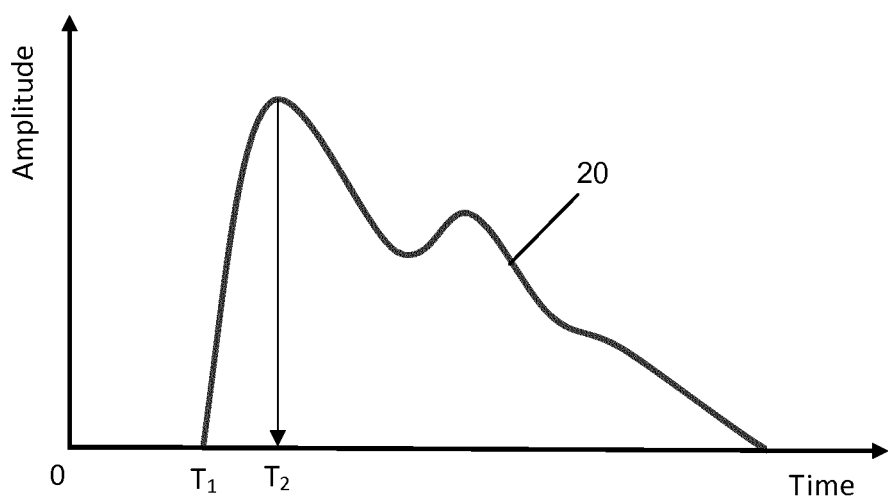
FIG. 2 shows a detected ultrasound pulse according to an embodiment.

In some embodiments the controller comprises a communications interface for enabling communication between the controller 10 and the transmitter 12 and between the controller 10 and the receiver 16. The controller also comprises a processing unit arranged to output a control signal to an ultrasound transmitter to cause the ultrasound transmitter to emit an ultrasound pulse; receive a measurement signal from an ultrasound receiver, corresponding to a detection by the receiver of the emitted ultrasound pulse; determine, based on the received measurement signal, $T_1$ and $T_2$, and calculate using $T_1$ and $T_2$ a flow velocity of blood in an blood vessel located between the transmitter and the receiver. Although FIG. 1 shows the controller 10 as separate from the transmitter 12 and the receiver 16, embodiments are envisaged in which the controller is integrated with either the transmitter or the receiver. Ultrasound waves (e.g. which have been emitted by the transmitter 12) which are travelling in the same direction as the flow of blood as they pass through the blood vessel between the transmitter 12 and receiver 16 will arrive at the receiver slightly earlier (i.e. at time $T_1$) than ultrasound waves that only travel through stationary blood or tissue (which will arrive at time $T_2$). For an unfocussed pulse of ultrasound, this difference in time-of-flight will be reflected in the shape of the detected pulse. FIG. 2 shows an example measurement signal 20 generated by a receiver, where the measurement signal corresponds to the envelope of a detected ultrasound pulse which has passed through a blood vessel in the direction of the blood flow and through surrounding tissue. The earliest arriving part of the pulse (i.e. the part which arrives at the receiver at time $T_1$) corresponds to ultrasound waves which have passed through blood flowing in the direction of the ultrasound pulse, the main part of the pulse (i.e. the part which arrives around time $T_2$) corresponds to ultrasound waves which have passed through stationary blood and tissue, and the tail of the pulse (i.e. the part which arrives after $T_2$) corresponds to ultrasound waves which have been reflected and refracted by anatomical structures.

Blood flow in the direction of the wave front (i.e. in the same direction as the direction of travel of the ultrasound waves) increases the speed of the wave front in proportion to the flow velocity, which means that amount of time by which the first part of the rising edge of the envelope of the detected pulse (i.e. the part of the pulse received before time $T_2$) precedes the main part of the envelope is proportional to the velocity and amount of blood flow in the direction of the wave front. Because the blood flow (and thus $T_1$) varies according to the cardiac cycle whereas $T_2$ is not affected by the cardiac cycle, the rising edge of the detected pulse envelope will deform relative to the main peak with each heartbeat.

The peak flow velocity corresponds to the maximum difference, over a complete cardiac cycle, between $T_1$ and $T_2$. Beat-to-beat variations in this peak flow velocity reflect the subject's blood volume status. Large variations are indicative of hypovolemia (decreased blood volume) and small variations are indicative of hypervolemia (fluid overload) or hypertension. Monitoring these variations would be particularly useful for the home monitoring of hypertensive patients and pregnant women at (e.g. because excessive salt intake increases the circulating volume and beat-to-beat hemodynamic variability, whilst diuretics decrease the circulating volume and beat-to-beat hemodynamic variability).

Thus, the difference between the time taken to reach the receiver by the earliest arriving ultrasound waves, and the time taken to reach the receiver by the main part of the ultrasound pulse (which equates to the difference between the arrival times at the receiver, since the transmission path is very similar) is caused by blood flow in the blood vessel and can be used to derive a time-varying signal for the flow velocity of this blood.

Various techniques can be used, e.g. by a processing unit of the controller 10, to determine the arrival times (e.g. $T_1$ and $T_2$) of different parts of a detected ultrasound pulse. In some embodiments the arrival time $T_1$ of the first part is defined as the time at which the signal envelope rises through a first predefined threshold amplitude and the arrival time $T_2$ of the main part is defined as the time at which the signal envelope rises through a second predefined threshold amplitude. In some such embodiments the first predefined threshold amplitude corresponds to a first percentage of the peak envelope amplitude and the second predefined threshold amplitude corresponds to a second, larger, percentage of the peak envelope amplitude. In some embodiments the first percentage is in the range 1-10%. In some embodiments the second percentage is in the range 50-100%. In some embodiments $T_1$ and $T_2$ are determined using, e.g., techniques based on a Constant Fraction Discriminator, shape fitting, or model parameter fitting.

Since the time at which a given pulse was emitted can be known, e.g. because it is the time at which the controller 10 sent a control signal causing the transmitter 12 to emit the pulse, which can be recorded by the controller 10, the time of flight of the first part of the pulse ($ToF_1$) and the time of flight of the main part of the pulse ($ToF_2$) can be calculated from $T_1$ and $T_2$ (i.e. using $ToF_1 = T_1 - T_0$, and $ToF_2 = T_2 - T_0$, where $T_0$ is the time at which the pulse was emitted). The velocity of blood flow in the blood vessel between the transmitter 12 and the receiver 16 can be determined from $ToF_1$ and $ToF_2$ in the following manner. If the ultrasound path between the transmitter 12 and the receiver 16 has length L and the sound travels at a known speed c (approximately 1540 m/s) through stationary blood or tissue, the time of flight $ToF_2$ for the main part of the ultrasound pulse corresponds to:

$$ToF_2 = \frac{L}{c}. \quad \text{(Equation 1)}$$

For ultrasound which has passed through blood flowing with velocity v in the direction of the sound, the time of flight $ToF_1$ is a slightly shorter and is given by:

$$ToF_1 = \frac{L}{c+v}. \quad \text{(Equation 2)}$$

L can be roughly estimated for a given subject, using Equation 1, which enables the unknown blood velocity v to be calculated from:

$$(T_2 - T_1)\frac{c^2}{L} = (ToF_2 - ToF_1)\frac{c^2}{L} = \frac{vc}{(c+v)} \approx v. \quad \text{(Equation 3)}$$

(The last approximation holds because v≪c).
However; it is often more convenient and more accurate to derive the unknown blood velocity v based on $ToF_1$ and $ToF_2$ directly without knowing path length L, using the following expression:

$$\frac{(ToF_2 - ToF_1)c}{ToF_2} = \frac{vc}{(c+v)} \approx v. \quad \text{(Equation 4)}$$

In both cases the actual blood velocity will be slightly higher than the calculated value because the sound travels through skin and some tissue before it reaches the flowing blood flow. In some embodiments a fixed correction factor is used to compensate for this effect. In some such embodiments the correction factor is determined in dependence on the size of the subject and/or on an estimate of L.

Figure 3:
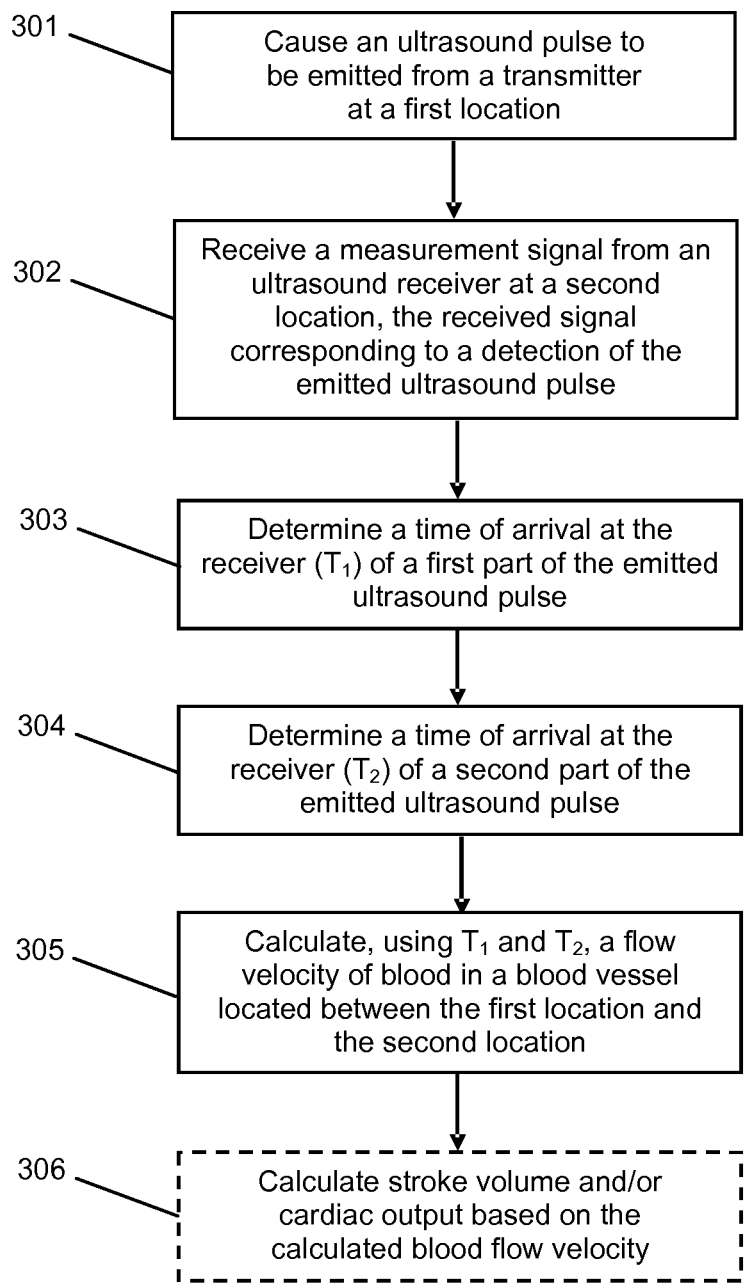
FIG. 3 is a flow chart of a method of measuring the velocity of blood flowing in a blood vessel of a subject according to an embodiment.

FIG. 3 shows a method of measuring the velocity of blood flowing in a blood vessel of a subject. The method can be implemented entirely by the controller 10 (e.g. by a processing unit of the controller 10). Alternatively, the controller 10 can transmit the received measurement signal to another device (such as a smart phone, laptop computer, desktop computer or other processing device) that comprises a controller suitable for processing the received measurement signal to produce flow velocity values and that implements steps 303-307 of the method shown in FIG. 3.

In a first step 301 an ultrasound pulse is caused to be emitted from a transmitter, e.g. the transmitter 12. In some embodiments causing the ultrasound pulse to be emitted comprises a controller (e.g. the controller 10) sending a control signal to the transmitter. In some embodiments the ultrasound pulse is caused to be emitted a predetermined amount of time after the emission of a previously emitted ultrasound pulse. In some embodiments the predetermined amount of time is in the range 0.1 ms to 0.1 s. The ultrasound pulse may have any or all of the features described above in relation to the transmitter 12.

The transmitter is arranged at a first location on the body of the subject. The first location is near a major blood vessel of the subject, in which it is desired to measure blood flow velocity. Preferably the blood vessel is an artery, e.g. the descending aorta. For example, if it is desired to measure blood flow velocity in the descending aorta, suitable first locations include the neck, left shoulder, mouth or oesophagus. Preferably the first location is as close as anatomically possible to the blood vessel. The transmitter may be attached to the subject at the first location using any suitable fixing mechanism such as straps, adhesive, etc., or may be held in place by the subject or by a healthcare professional. In preferred embodiments, the transmitter is a wide-angle transmitter, so that it does not need to be accurately aimed at the receiver.

In a second step 302, a measurement signal is received, e.g. by the controller 10, from an ultrasound receiver (e.g. the receiver 16). The measurement signal corresponds to detection by the receiver of the ultrasound pulse emitted in step 301. In some embodiments the measurement signal comprises a time-series of amplitude values.

The receiver is arranged at a second location on the body of the subject. The second location is selected such that the blood vessel in which it is desired to measure blood flow is between the transmitter and the receiver. In embodiments in which a wide-angle transmitter and a wide-angle receiver are used, the blood vessel need not be exactly on the line of sight between the transmitter and receiver. The second location is selected such that at least some of the ultrasound waves emitted by the transmitter at the first location and subsequently detected by the receiver will have been travelling in the same direction as the flow of blood in the blood vessel when they passed through the blood vessel (i.e. the second location is downstream from the first location, with respect to the main blood flow in the blood vessel). For example, if it is desired to measure blood flow velocity in the descending aorta, suitable second locations could be found on the back of the subject, preferably under the ribcage and aside from the spine. Preferably the second location is as close as anatomically possible to the blood vessel. Preferably the separation between the first and second locations is as large as possible. The receiver may be attached to the subject at the second location using any suitable fixing mechanism such as straps, adhesive, etc., or may be held in place by the subject or by a healthcare professional. In preferred embodiments, the receiver is a wide-angle receiver, so that it does not need to be accurately aimed at the transmitter.

In step 303, a time of arrival at the receiver ($T_1$) of a first part of the emitted ultrasound pulse is determined, based on the received measurement signal. In some embodiments the first part corresponds to a rising edge (i.e. a first rising edge) of an envelope of the measurement signal. In some embodiments the first part corresponds to the part of the signal which arrives at the receiver earliest. In some embodiments the first part does not correspond to a main peak of an envelope of the measurement signal. In some embodiments at least one criterion which defines the first part and/or $T_1$ is used in determining $T_1$. The at least one criterion may be stored, for example, in a memory of the controller implementing the method. In some embodiments $T_1$ is defined as the time at which the signal envelope rises through a first predefined threshold amplitude and determining $T_1$ comprises determining the earliest time at which the signal amplitude exceeds the first predefined threshold. In some such embodiments the first predefined threshold amplitude corresponds to a first percentage of the peak envelope amplitude. In some embodiments the first percentage is in the range 1-10%. In some embodiments $T_1$ is determined using, e.g., techniques based on a Constant Fraction Discriminator, shape fitting, or model parameter fitting.

In step 304 a time of arrival at the receiver ($T_2$) of a second part of the emitted ultrasound pulse is similarly determined, based on the received measurement signal. In some embodiments the second part comprises a main peak of an envelope of the measurement signal. In some embodiments the second part comprises a section of the received signal immediately before the main peak. In some embodiments at least one criterion which defines the second part and/or $T_2$ is used in determining $T_2$. The at least one criterion may be stored, for example, in a memory of the controller implementing the method. In some embodiments $T_2$ is defined as the time at which the signal envelope rises through a second predefined threshold amplitude and determining $T_2$ comprises determining the earliest time at which the signal amplitude exceeds the second predefined threshold. In some such embodiments the second predefined threshold amplitude corresponds to a larger percentage of the peak envelope amplitude than the first predefined threshold amplitude. In some embodiments the second percentage is in the range 50-100%. In some embodiments $T_2$ is determined using, e.g., techniques based on a Constant Fraction Discriminator, shape fitting, or model parameter fitting.

Then, in step 305, a flow velocity of blood in a blood vessel located between the first location and the second location (i.e. between the transmitter and the receiver) is calculated, e.g. by the controller 10. Any of the techniques described above for deriving the flow velocity may be used in the performance of step 305.

In some embodiments the method includes an additional optional step 306 of calculating the stroke volume and/or cardiac output of the subject, based on the calculated blood flow velocity. First, the time-dependent velocity value is converted into a blood flow value using:

$$F = fvD^2\left(\frac{\pi}{4}\right) \quad \text{(Equation 5)}$$

where F is the blood flow, f is a fixed constant that corrects for the velocity profile (i.e. the fact that in general, blood velocity in the center of a blood vessel's cross-section is higher than blood velocity near the vessel walls) and the fraction of the blood that flows through early branches of the blood vessel, and D is the diameter of the blood vessel. Constant f can be determined experimentally, e.g. by measuring cardiac output or stroke volume using a different methodology, or can be calculated in cases where the velocity profile is known. The value of f is expected to be very similar for all subjects, and therefore need not be determined on a subject-by-subject basis. D can be measured from one-time images of the blood vessel (obtained, e.g., using ultrasound, MRI, or CT), or estimated based on the age, weight and/or height of the subject.

The flow F can then be converted into stroke volume or cardiac output by integrating F as a function of time over a single heartbeat (for stroke volume) or over a minute (for cardiac output). However; various clinical applications are envisaged which do not require the calculation of stroke volume or cardiac output. Since blood velocity is directly proportional to flow, the calculated velocity values can be used directly in situations where the velocity signal can be calibrated against a one-time cardiac measurement (e.g. obtained using a catheter). The calculated velocity values can also be used to track trends, or to measure the relative response of a subject to a fluid challenge. A fluid challenge comprises a test which can determine the fluid responsiveness of a subject, such as raising the subject's leg, or giving the subject an intravenous infusion of a significant volume of saline.

In some embodiments the method is performed continuously, such that ultrasound pulses are caused to be emitted at regular intervals and a blood flow velocity value is calculated in respect of each emitted pulse. In such embodiments the pulses may be emitted at a frequency in the range 10 Hz to 10 kHz. Preferably the repetition frequency of the pulses is high enough to permit variations of blood flow velocity caused by the cardiac cycle to be tracked. In embodiments where the method is performed continuously over multiple cardiac cycles, the output comprises a time-series of blood flow velocity values, in other words a velocity signal (or, if step 306 is performed, a stroke volume or cardiac output signal). Advantageously, this enables beat-to-beat variations (e.g. of peak blood flow velocity or stroke volume) to be detected and tracked. The magnitude of such variations is relevant to several clinical conditions, as discussed above.

In some such embodiments, the velocity signal is processed. In some embodiments this processing comprises filtering the velocity signal, e.g. using a band pass filter. For example, filtering variations synchronous with the subject's heartbeat rhythm using a band pass filter facilitates distinguishing blood flow information from noise and from variations caused by body motion. In some embodiments data from an independent heartbeat detector, such as an electrocardiograph (ECG) or a photoplethysmograph (PPG), is used to synchronize the filtering to the subject's heartbeats. In some embodiments an ECG and/or PPG is integrated into the transmitter 12 or the receiver 16. Preferably filtering of variations synchronous with the subject's heartbeat rhythm is performed on a signal which covers several cardiac cycles.

In some embodiments the processing of the velocity signal comprises fitting the velocity signal to a model, e.g. a model of a cardiac flow signal. In some such embodiments the fitting comprises fitting the shape of the velocity signal to a model. In some such embodiments the fitting comprises fitting the frequency of the velocity signal to a model. Fitting the received measurement signal to a model facilitates noise cancellation, and consequently can improve the signal-to-noise ratio (SNR) of the received signal. A model of the cardiac flow signal for use in noise reduction can be estimated by detecting, in the velocity signal, the zero flow moments of the cycle (i.e. the brief periods between heartbeats when the flow is zero, or nearly zero).

In some embodiments processing the velocity signal comprises applying a filter or correction factor to the velocity signal based on body posture information. Such body posture information can be obtained, for example, using one or more accelerometers. In some embodiments an accelerometer is integrated into the transmitter and/or the receiver. Arterial blood flow is affected by gravity, so correcting the velocity signal for body posture can eliminate artefacts resulting from gravitational effects. Preferably reduction/removal of posture related artefacts is performed on a velocity signal which covers several cardiac cycles.

In embodiments in which step 306 is performed, a stroke volume signal or cardiac output signal may be processed using similar techniques to those described above in relation to the velocity signal.

Useful information can be obtained by measuring blood flow velocity in the reverse direction, e.g. performing a measurement with the transmitter arranged at the second location and the receiver located at the first location. In some embodiments, therefore, the method of FIG. 3 includes the additional steps (not shown) of causing a further ultrasound pulse to be emitted from an ultrasound transmitter at the second location; receiving a further measurement signal from an ultrasound receiver at the first location, the received further signal corresponding to a detection by the receiver of the emitted further ultrasound pulse; determining, based on the received further measurement signal, a time of arrival at the receiver at the first location, $Tf_1$, of a first part of the emitted further ultrasound pulse; determining, based on the received further measurement signal, a time of arrival at the receiver at the first location, $Tf_2$, of a second part of the emitted further ultrasound pulse; and calculating, using $Tf_1$ and $Tf_2$, a further flow velocity of blood in an blood vessel located between the first location and the second location, where the further flow velocity is of blood flowing in the opposite direction to the calculated flow velocity. For example, if in steps 301-305 the downwards blood flow velocity in the descending aorta is determined, measuring in the reverse direction as described above will yield flow velocity information for blood flowing upwardly in or near the aorta (i.e. blood in the inferior vena cava and back flow in the descending aorta).

In some embodiments a calibration process is performed prior to performing the method of FIG. 3. In some such embodiments one or more parameters of the transmitter are adjusted through a predetermined range whilst one or more attributes of the received signal (e.g. amplitude, signal-to-noise ratio, etc.) are measured. The parameter or combination of parameters which yields the best signal attributes is then selected to be an operational parameter of the transmitter. The parameter may comprise, for example, location, angle, beam direction, beam focus, etc. In embodiments in which the transmitter includes an electronic beam steering capability and/or an electronic focusing capability, such capabilities may be used to alter parameters of the transmitter during a calibration process. An equivalent process may be performed in respect of the receiver. The transmitter and/or receiver may be calibrated each time the transmitter and receiver are arranged on a subject. In some embodiments (i.e. embodiments in which at least one of the transmitter and receiver has electronic beam steering and/or focusing capabilities) the calibration process is performed automatically, e.g. it is implemented by the controller 10.

Embodiments of the invention therefore provide a low-cost and non-invasive method for measuring beat-to-beat aortic or arterial blood flow velocity, and the variability thereof. Such measurements can be used to assess a subject's fluid volume status and fluid responsiveness, and can furthermore provide an early warning for hemodynamic instability. The embodiments can therefore be highly useful in various clinical settings, including in the emergency room, general ward, intensive care unit, and operating room. Embodiments of the invention can also be used for home monitoring, e.g. of subjects at risk of hypovolemia (such as elderly people, who often become hypovolemic through dehydration), pregnant women and/or hypertensive subjects.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for measuring flow velocity of blood flowing in a blood vessel of a subject, the apparatus comprising:
    an ultrasound transmitter, for placement at a first location on the body of a subject, and arranged to emit an ultrasound pulse;
    an ultrasound receiver, for placement at a second location on the body of the subject, and arranged to detect an ultrasound pulse emitted by the ultrasound transmitter; and
    a controller in communication with the ultrasound transmitter and the ultrasound receiver and arranged to:
        cause an ultrasound pulse to be emitted by the ultrasound transmitter;
        receive a measurement signal from the ultrasound receiver corresponding to the ultrasound pulse;
        determine $T_1$, based on the received measurement signal, wherein $T_1$ is a time of arrival at the ultrasound receiver of a first part of the emitted ultrasound pulse;

determine $T_2$, based on the received measurement signal, wherein $T_2$ is a time of arrival at the ultrasound receiver of a second part of the emitted ultrasound pulse; and calculate, using $T_1$ and $T_2$, the flow velocity of the blood flowing in the blood vessel located between the first location and the second location, wherein the flow velocity is calculated from:

$$\frac{(ToF_2 - ToF_1)c}{ToF_2} = \frac{vc}{(c+v)} \approx v$$

where $ToF_1$ is a time of flight of the first part of the emitted ultrasound pulse and is given by $ToF_1 = T_1 - T_0$ and $$ToF_1 = \frac{L}{c+v},$$

$ToF_2$ is a time of flight of the second part of the emitted ultrasound pulse and is given by $ToF_2 = T_2 - T_0$ and $$ToF_2 = \frac{L}{c},$$

L is the length of the ultrasound path between the ultrasound transmitter and the ultrasound receiver, v is the flow velocity, C is the speed of sound in soft tissue, and $T_0$ is a time at which the ultrasound pulse was emitted;

or is calculated from:

$$(T_2 - T_1)\frac{c^2}{L} = \frac{vc}{(c+v)} \approx v.$$

2. The apparatus of claim 1, wherein the first part of the emitted ultrasound pulse corresponds to at least part of a first rising edge of an envelope of the received measurement signal and the second part of the emitted ultrasound pulse corresponds to at least part of a main peak of the envelope.

3. The apparatus of claim 1, wherein determining $T_1$ comprises determining an earliest time at which the envelope of the received measurement signal equals a first predefined threshold amplitude and determining $T_2$ comprises determining the earliest time at which the envelope of the received measurement signal equals a second predefined threshold amplitude.

4. The apparatus of claim 3, wherein the first predefined threshold amplitude corresponds to a first percentage of a maximum amplitude of the received measurement signal and the second predefined threshold amplitude corresponds to a second percentage of the maximum amplitude, wherein the second percentage of the maximum amplitude is larger than the first percentage of the maximum amplitude.

5. The apparatus of claim 1, wherein the controller is arranged to:
cause the ultrasound pulse to be emitted by the ultrasound transmitter at regular intervals;
receive the measurement signal from the ultrasound receiver, determine $T_1$ and $T_2$, and calculate the flow velocity, in respect of each emitted ultrasound pulse; and
generate a time-dependent flow velocity signal based on the calculated flow velocity values.

6. The apparatus of claim 5, wherein the controller is further arranged to:
receive a heartbeat rhythm signal for the subject; and
filter the time-dependent flow velocity signal to extract variations synchronous with the received heartbeat rhythm signal using a band pass filter.

7. The apparatus of claim 5, wherein the controller is further arranged to fit the time-dependent flow velocity signal to a model.

8. The apparatus of claim 5, wherein the controller is further arranged to:
receive posture information for the subject; and
correct the flow velocity signal based on the received posture information.

9. The apparatus of claim 5, wherein the controller is further arranged to calculate a stroke volume and/or a cardiac output of the subject, based on the flow velocity of the blood.

10. The apparatus of claim 1, wherein one or more operational parameters of the ultrasound transmitter and/or the ultrasound receiver is automatically adjustable by the controller, and wherein the controller is further arranged to perform a calibration process comprising:
adjusting one or more operational parameters of the ultrasound transmitter and/or the ultrasound receiver;
measuring one or more attributes of the measurement signal received from the ultrasound receiver; and
selecting a value for each of the one or more operational parameters of the ultrasound transmitter and/or the ultrasound receiver based on the measured one or more attributes.

11. The apparatus of claim 10, wherein the blood vessel comprises the descending aorta of the subject.

12. The apparatus of claim 1, wherein each of the ultrasound transmitter and the ultrasound receiver comprises circuitry embedded in an adhesive patch for adhering to a surface of the subject.

13. The apparatus of claim 1, the controller comprises:
a communications interface for enabling communication between the controller and ultrasound transmitter and between the controller and the ultrasound receiver.

14. The apparatus of claim 1, wherein the blood vessel comprises the descending aorta of the subject.

15. The apparatus of claim 1, wherein calculating the flow velocity of the blood flowing in the blood vessel comprises calculating, using $T_1$ and $T_2$, the flow velocity of the blood in the blood vessel located between the ultrasound transmitter and the ultrasound receiver.

16. A method of measuring flow velocity of blood flowing in a blood vessel of a subject, the method comprising:
causing an ultrasound pulse to be emitted from an ultrasound transmitter at a first location on the body of the subject;
receiving a measurement signal from an ultrasound receiver at a second location on the body of the subject, the received signal corresponding to a detection by the ultrasound receiver of the ultrasound pulse;
determine $T_1$, based on the received measurement signal, wherein $T_1$ is a time of arrival at the ultrasound receiver of a first part of the emitted ultrasound pulse;
determine $T_2$, based on the received measurement signal, wherein $T_2$ is a time of arrival at the ultrasound receiver of a second part of the emitted ultrasound pulse; and
calculating, using $T_1$ and $T_2$, the flow velocity of blood flowing in the blood vessel located between the first location and the second location, wherein the flow velocity is calculated from:

$$\frac{(ToF_2 - ToF_1)c}{ToF_2} = \frac{vc}{(c+v)} \approx v$$

wherein $ToF_1$ is a time of flight of the first part of the emitted ultrasound pulse and is given by $ToF_1 = T_1 - T_0$ and $$ToF_1 = \frac{L}{c+v},$$

$ToF_2$ is a time of flight of the second part of the emitted ultrasound pulse and is given by $ToF_2 = T_2 - T_0$ and $$ToF_2 = \frac{L}{c},$$

L is the length of the ultrasound path between the ultrasound transmitter and the ultrasound receiver, v is the flow velocity, c is the speed of sound in soft tissue, and $T_0$ is a time at which the ultrasound pulse was emitted;

or is calculated from:

$$(T_2 - T_1)\frac{c^2}{L} = \frac{vc}{(c+v)} \approx v.$$

17. The method of claim 16, wherein the blood vessel comprises the descending aorta of the subject.

* * * * *